United States Patent [19]

Böckmann et al.

[11] Patent Number: 4,845,116
[45] Date of Patent: Jul. 4, 1989

[54] 1-(2,4-DIFLUOROPHENYL)-1-(1-FLUOROCYLOPROPYL)-2-(1,2,4-TRIAZOL-1-YL)-ETHAN-1-OL

[75] Inventors: Klaus Böckmann, Cologne; Klaus Stroech, Solingen; Stefan Dutzmann, Duesseldorf; Paul Reinecke, Leverkusen, all of Fed. Rep. of Germany

[73] Assignee: Bayer Aktiengesellschaft, Leverkusen, Fed. Rep. of Germany

[21] Appl. No.: 150,684

[22] Filed: Feb. 1, 1988

[30] Foreign Application Priority Data

Feb. 12, 1987 [DE] Fed. Rep. of Germany ....... 3704261

[51] Int. Cl.$^4$ ................. A01N 43/653; C07D 249/08
[52] U.S. Cl. .................................... 514/383; 548/262
[58] Field of Search ......................... 514/383; 548/262

[56] References Cited

FOREIGN PATENT DOCUMENTS 3440116 5/1986 Fed. Rep. of Germany .
3535456 5/1986 Fed. Rep. of Germany .

Primary Examiner—Glennon H. Hollrah
Assistant Examiner—Patricia L. Morris
Attorney, Agent, or Firm—Sprung Horn Kramer & Woods

[57] ABSTRACT 1-(2,4-Difluorophenyl)-1-(1-fluorocylopropyl)-2-(1,2,4,-triazol-1-yl)-ethan- 1-ol of the formula

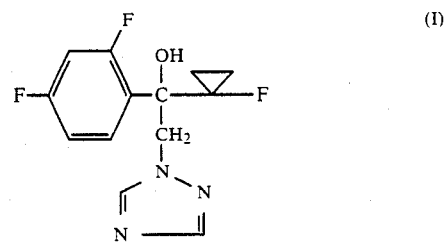

is active against Pseudocercosporella herpotrichoides and is produced by the following reaction sequence:

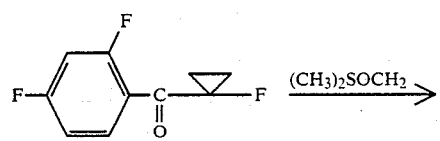

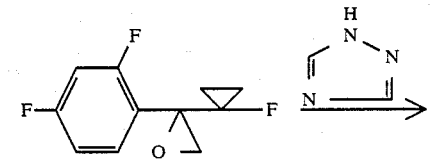

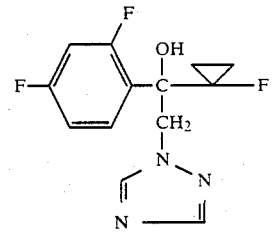

3 Claims, No Drawings

1-(2,4-DIFLUOROPHENYL)-1-(1-FLUOROCYLOPROPYL)-2-(1,2,4-TRIAZOL-1-YL)-ETHAN-1-OL

The present invention relates to the new compound 1-(2,4-difluorophenyl)-1-(1-fluorocyclopropyl)-2-(1,2,4-triazol-1-yl)-ethan-1-ol, a process for its preparation and its use for combating *Pseudocercosporella herpotrichoides*.

It has already been disclosed that certain azolylmethyl-cyclopropyl-carbinol derivatives have a good fungicidal activity (compare EP-OS (European Published Specification) No. 0,180,136). However, a specific use of these substances against *Pseudocercosporella herpotrichoides* has not yet been described.

It is furthermore already known that N-[2-(2,4,6-trichlorophenoxy)-ethyl]-N-propyl-1H-imidazole-1-carboxamide is suitable for combating *Pseudocercosporella herpotrichoides* (compare U.S. Pat. Nos. 3,991,071 and 4,080,462). However, when low amounts are applied, the effectiveness of this substance is not always satisfactory.

The new compound 1-(2,4-difluorophenyl)-1-(1-fluorocyclopropyl)-2-(1,2,4-triazol-1-yl)-ethan-1-ol of the formula

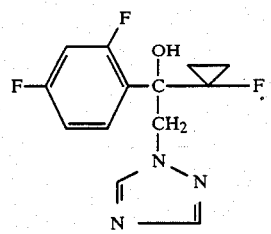

(I)

has now been found.

It has furthermore been found that the new compound 1-(2,4-difluorophenyl)-1-(1-fluorocyclopropyl)-2-(1,2,4-triazol-1-yl)-ethan-1-ol of the formula (I) is obtained by a process in which (a) in a first stage, 2,4-difluorophenyl 1-fluorocyclopropyl ketone of the formula

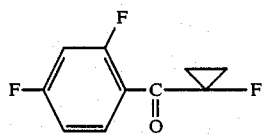

(II)

is reacted either (α) with dimethyloxosulphonium methylide of the formula

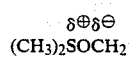

(III)

or (β) with dimethylsulphonium methylide of the formula

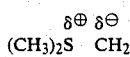

(IV)

in the presence of a diluent and (b) in a second stage, the 1-(2,4-difluorophenyl)-1-(1-fluoro-cyclopropyl)-oxirane thereby formed, of the formula

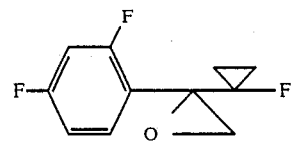

(V)

is reacted with 1,2,4-triazole of the formula

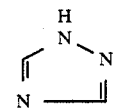

(VI)

in the presence of an acid-binding agent and in the presence of a diluent.

Finally, it has been found that the new compound 1-(2,4-difluorophenyl)-1-(1-fluorocyclopropyl)-2-(1,2,4-triazol-1-yl)-ethan-1-ol of the formula (I) is particularly suitable for combating *Pseudocercosporella herpotrichoides*.

Suprisingly, the active compound of the formula (I) according to the invention shows a considerably better activity when used against *Pseudocercosporella herpotrichoides* than N-[2-(2,4,6-trichlorophenoxy)-ethyl]-N-propyl-1H-imidazole-carboxamide, which is recognized as a particularly effective and chemically similar active compound of the same type of action.

If dimethyloxosulponium methylide is used as the generator of methylene in carrying out the process according to the invention, the course of the process can be illustrated by the following equation:

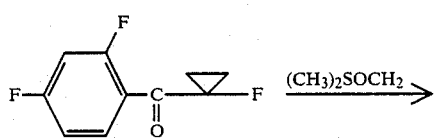

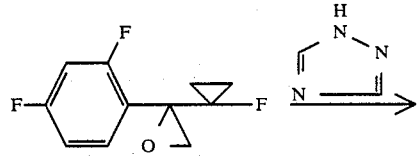

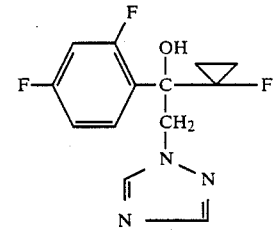

The 2,4-difluorophenyl 1-fluorocyclopropyl ketone of the formula (II) required as the starting substance for the process according to the invention is as yet not known. It can be prepared by a process in which 2,4-difluorophenyl 3-chloro-1-fluoro-propyl ketone of the formula

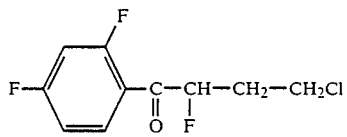

is reacted in the presence of an acid-binding agent and in the presence of a diluent.

The 2,4-difluorophenyl 3-chloro-1-fluoro-propyl ketone of the formula (VII) required as the starting substance in the above process can be prepared by a process in which 2,4-difluorophenyl 1-bromo-3-chloro-propyl ketone of the formula

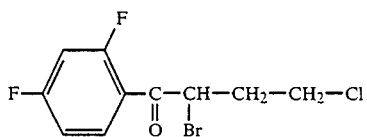

is reacted with sodium fluoride or potassium fluoride in the presence of an inert organic diluent, such as, for example, benzene, and in the presence of a complexing agent, such as, for example, 18-crown-6, at temperatures between 20° and 150° C.

Possible acid-binding agents in the above process for the preparation of the compound of the formula (II) are all the customary inorganic and organic bases. Bases which can preferably be used are alkali metal carbonates, such as sodium carbonate and potassium carbonate, alkali metal hydroxides, such as sodium hydroxide and potassium hydroxide, alkali metal alcoholates, such as sodium methylate, ethylate and tert.-butylate and potassium methylate, ethylate and tert.-butylate; alkali metal hydrides, such as sodium hydride, and lower tertiary alkylamines, cycloalkylamines and aralkylamines, such as, in particular, triethylamine.

All the organic solvents which are inert under the reaction conditions can be used as the diluent in the above process for the preparation of the compound of the formula (II). Solvents which can preferably be used are alcohols, such as methanol, ethanol, methoxyethanol, propanol or tert.-butanol, and furthermore ketones, such as acetone and 2-butanone, and also nitriles, such as acetonitrile, and moreover esters, such as ethyl acetate, and in addition ethers, such as dioxane, aromatic hydrocarbons, such as benzene or toluene and also amides, such as dimethylformamide.

The reaction temperatures can be varied within a substantial range in carrying out the above process for the preparation of the compound of the formula (II). The reaction is in general carried out at temperatures between 0° C. and 200° C., preferably between 20° C. and 150° C.

In the preparation of the compound of the formula (II) by the above process, 1 to 2 mols of base are preferably employed per mol of 2,4-difluorophenyl 3-chloro-1-fluoro-propyl ketone of the formula (VII). The compound of the formula (II) is isolated in the customary manner.

The dimethyloxosulphonium methylide of the formula (III) required as a reaction component in the process according to the invention is known (compare J. Am. Chem. Soc. 87, 1363–1364 (1965)). It is processed in the freshly prepared state in the above reaction, in that it is generated in situ by the reaction of trimethyloxosulphonium iodide with sodium hydride or sodium amide, in particular with potassium tert.-butylate or sodium methylate, in the presence of a diluent.

The dimethylsulphonium methylide of the formula (IV) also suitable as a reaction component in the process according to the invention is likewise known (compare Heterocycles 8, 397 (1977)). It is likewise used in the freshly prepared state in the above reaction, in that it is generated in situ, for example from a trimethylsulphonium halide or trimethylsulphonium methylsulphate in the presence of a strong base, such as, for example, sodium hydride, sodium amide, sodium methylate, potassium tert.-butylate or potassium hydroxide, in the presence of a diluent, such as tert.-butanol or dimethylsulphoxide.

The 1-(2,4-difluorophenyl)-1-(1-fluorocyclopropyl)-oxirane of the formula (V) which arises as an intermediate in the process according to the invention is not yet known.

Possible diluents in carrying out the first stage of the process according to the invention are inert organic solvents. Solvents which can preferably be used are alcohols, such as tert.-butanol, ethers, such as tetrahydrofuran or dioxane, and furthermore aliphatic and aromatic hydrocarbons, such as benzene, toluene or xylene, as well as strongly polar solvents, such as dimethylsulphoxide.

The reaction temperatures can be varied within a substantial range in carrying out the first stage of the process according to the invention. The reaction is in general carried out between 0° and 100° C., preferably between 10° and 60° C.

In carrying out the first stage of the process according to the invention, preferably 1 to 3 mols of dimethyloxosulphonium methylide of the formula (III) or dimethylsulphonium methylide of the formula (IV) are employed per mol of 2,4-difluorophenyl 1-fluorocyclopropyl ketone of the formula (II). The intermediate of the formula (V) is isolated by customary methods.

The second stage of the process according to the invention is carried out in the presence of a base. All the inorganic and organic bases which can usually be employed are suitable here. Bases which can preferably be used are alkali metal carbonates, such as, for example, sodium carbonate and potassium carbonate; alkali metal hydroxides, such as, for example, sodium hydroxide; alkali metal alcoholates, such as, for example, sodium methylate and ethylate and potassium methylate and ethylate; alkali metal hydrides, such as, for example, sodium hydride, and lower tertiary alkylamines, cycloalkylamines and aralkylamines, such as, in particular, triethylamine.

Possible diluents for the second stage of the process according to the invention are inert organic solvents. Solvents which can preferably be used are nitriles, such as, in particular, acetonitrile; aromatic hydrocarbons, such as benzene, toluene and dichlorobenzene; formamides, such as, in particular, dimethylformamide, and hexamethylphosphoric acid triamide.

The reaction temperatures can be varied within a substantial range in carrying out the second stage of the process according to the invention. The process is in general carried out at temperatures between 0° C. and 200° C., preferably between 60° C. and 150° C.

In carrying out the second stage of the process according to the invention, 1 to 2 mols of 1,2,4-triazole and 1 to 2 mols of base are preferably employed per mol of oxirane of the formula (V). The end product is isolated in the customary manner.

The active compound according to the invention is outstandingly suitable for combating *Pseudocercosporella herpotrichoides*, the causative organism of stem break disease in cereals. The active compound according to the invention is preferably used for combating *Pseudocercosporella herpotrichoides* in wheat and barley.

The active compound can be converted to the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules or organic material such as sawdust, coconut shells, corn cobs and tobacco stalks; as emulsifying and/or foam-forming agents there are suitable: for example non-ionogenic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or lactices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations is general contain between 0.1 and 95 percent by weight of active compound, preferably between 0.5 and 90%.

The active compound according to the invention can be present in the formulations as a mixture with other known active compounds, such as fungicides, insecticides, acaricides and herbicides, as well as in mixtures with fertilizers and growth regulators.

The active compound can be used as such or in the form of its formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The preparation and use of the active compound according to the invention can be seen from the following examples.

PREPARATION EXAMPLE

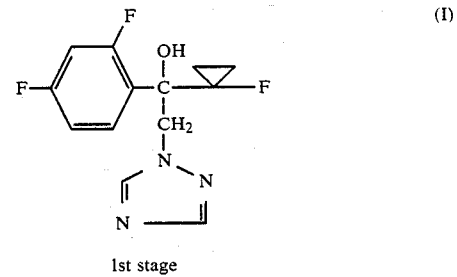

1st stage

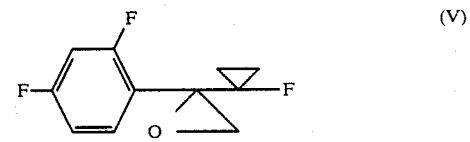

60 ml of absolute dimethylsulphoxide are added dropwise to a mixture of 2.3 g (77 mmol) of sodium hydride (80% strength) and 16.2 g (74 mmol) of trimethyloxosulphonium iodide under a nitrogen atmosphere at 10° C. The mixture is subsequently stirred for 1 hour and a solution of 13 g (65 mmol) of 2,4-difluorophenyl 1-fluorocyclopropyl ketone in 20 ml of absolute dimethylsulphoxide is then added dropwise. The mixture is left to stand at 20° C. for 2 days and then warmed to 40° C. for 1 hour and poured into water. The mixture formed is extracted several times with ethyl acetate and the combined organic phases are dried over sodium sulphate and concentrated by stripping off the solvent under reduced pressure. 13 g (94% of theory) of 1-(2,4-difluorophenyl)-1-(1-fluorocyclopropyl)-oxirane are obtained in this manner.

$^1$H-NMR (60 MHz, CDCl$_3$): δ=0.7–1.5 (m, 4H), 2.8–3.2 (m, 2H), 6.5–7.1 (m, 2H), 7.2–7.6 (m, 1H).

2nd stage

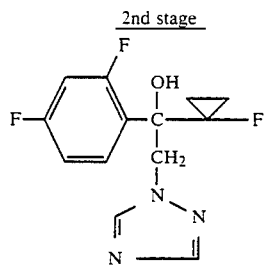
(I)

A solution of 13 g (61 mmol) of 1-(2,4-difluorophenyl)-1-(1-fluorocyclopropyl)-oxirane in 20 ml of absolute dimethylformamide is added dropwise to a mixture of 14 g (200 mmol) of 1,2,4-triazole and 1.7 g (15 mmol) of potassium tert.-butylate in 50 ml absolute dimethylformamide at 80° C., while stirring. The mixture is heated at 80° C. for a further 8 hours, while stirring, and the solvent is then stripped off under reduced pressure. The residue which remains is taken up in ethyl acetate. The solution formed is washed with water, dried over sodium sulphate and concentrated by stripping off the solvent under reduced pressure. The product which remains is purified by chromatography on a silica gel column (mobile phase: chloroform). After the eluate has been evaporated, 9 g (52% of theory) of 1-(2,4-difluoro-phenyl)-1-(1-fluorocyclopropyl)-2-(1,2,4-triazol-1-yl)-ethan-1-ol, which has a melting point of 112° C. after recrystallization from cyclohexane, are obtained.

Preparation of the precursors:

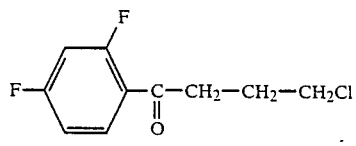

255 g (1.81 mols) of 4-chlorobutyryl chloride are added dropwise to a mixture of 200 g (1.75 mols) of 1,3-difluorobenzene and 256 g (1.92 mols) of anhydrous aluminum chloride at room temperature, while stirring. The mixture is stirred at 30° C. for 4 hours and then poured onto 1,200 g of ice. 1,200 ml of methylene chloride are added, the organic phase is separated off, the aqueous phase is extracted with methylene chloride and the combined organic phases are washed with water, dried over sodium sulphate and concentrated by stripping off the solvent under reduced pressure. The residue which remains is distilled. 326 g (85% of theory) of 2,4-difluorophenyl 3-chloropropyl ketone are obtained in this manner.

Boiling point: 92° C./0.2 mbar

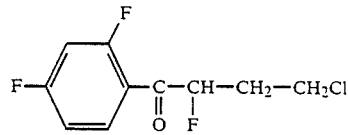
(VIII)

A solution of 410.7 g (2.57 mols) of bromine in 400 ml of methylene chloride is added dropwise to a solution of 555 g (2.54 mols) of 2,4-difluorophenyl 3-chloropropyl ketone in 1,100 ml of methylene chloride at room temperature, while stirring. The mixture is subsequently stirred at room temperature for 1 hour. The solvent is then stripped off under reduced pressure. 715 g (95% of theory) of 2,4-dilfuorophenyl 1-bromo-3-chloro-propyl ketone are obtained in this manner.

$^1$H-NMR (60 MHz, CDCl$_3$): =2.4–2.85 (m, 2H), 3.5–4.0 (m, 2H), 5.5 (dd, 1H), δ6.8–7.3 (m, 2H), 7.9–8.3 (m, 1H).

(VII)

450 ml of absolute benzene and 24.5 g of 18-crown-6 are added to 61 g of potassium fluoride dried under an oil pump at 150° C. 150 g (0.5 mol) of 2,4-difluorophenyl 1-bromo-3-chloropropyl ketone are added and the mixture is heated under reflux for 8 hours. After cooling, 250 ml of ethyl acetate are added, the organic phase is washed three times with water and dried over sodium sulphate and the solvent is distilled off. 135 g of 2,4-difluorophenyl 3-chloro-1-fluoropropyl ketone, which is further reacted without additional purification, are obtained.

135 g of 2,4-difluorophenyl 3-chloro-1-fluoropropyl ketone are added dropwise to a mixture of 85 g (0.75 mol) of potassium tert.-butylate and 240 ml of tert.-butanol at 40° C., while stirring. The reaction mixture is stirred at 40° C. for 2 hours and then poured onto 500 g of ice. The mixture formed is extracted three times with 250 ml of ethyl acetate each time and the combined organic phases are washed twice with water, dried over sodium sulphate and concentrated by stripping off the solvent under reduced pressure. Distillation of the residue which remains gives 13.3 g (13.3% of theory; based on the 2,4-difluorophenyl 1-bromo-3-chloro-propyl ketone) of 2,4-difluorophenyl 1-fluorocyclopropyl ketone.

Boiling point: 78° C./0.2 mbar

EXAMPLE A

Pseudocercosporella test (cereals)/shoot treatment field experiment

Cereal variety: Winter wheat
Plot size: 1 m$^2$
Number of repetitions: 3
Infestation by: *Pseudocercosporella herpotrichoides*

The active compounds are used in commercially available formulations when the cereal shoots.

Evaluation is carried out at the time at which the disease symptoms are complete and easy to recognise.

The active compounds, active compound concentrations and experimental results can be seen from the following table:

TABLE A

Pseudocerosporella test (cereals)/shoot treatment

| Field experiment Active compound | Amount of active compound applied in g/ha | Disease infestation in % of the untreated control |
|---|---|---|
| known: (A) 2,4,6-trichlorophenoxyethyl-N-ethyl-N-(vinyl-imidazol-1-yl-carbonyl)amine | 250 | 84.1 |
| according to the invention: 1-(2,4-difluorophenyl)-1-(1-fluorocyclopropyl)-2-(1,2,4-triazol-1-yl)-ethan-1-ol | 250 | 38.8 |

It will be appreciated that the instant specification and examples are set forth by way of illustration and not limitation, and that various modifications and changes may be made without departing from the spirit and scope of the present invention.

What is claimed is:

1. 1-(2,4-Difluorophenyl)-1-(1-fluorocyclopropyl)-2-(1,2,4-triazol-1-yl)-ethan-1-ol of the formula (I)

2. A composition for combating *Pseudocercosporella herpotrichoides* comprising an amount effective therefor of 1-(2,4-difluorophenyl)-1-(1-fluorocyclopropyl)-2-(1,2,4-triazol-1-yl)-ethan-1-ol according to claim 1 and a diluent.

3. A method of combating *Pseudocercosporella herpotrichoides* comprising applying thereto or to a locus from which it is desired to exclude such fungi an amount effective therefor of 1-(2,4-difluorophenyl)-1-(1-fluorocycloprop-1)-2-(1,2,4-triazol-1-yl)-ethan-1-ol according to claim 1.

* * * * *